United States Patent
Roby et al.

(10) Patent No.: US 10,675,074 B2
(45) Date of Patent: Jun. 9, 2020

(54) POROUS FIXATION DEVICES AND METHODS

(71) Applicant: Zimmer, Inc., Warsaw, IN (US)

(72) Inventors: Keith A. Roby, Jersey City, NJ (US);
John Chernosky, Brick, NJ (US);
Imants Liepins, Asbury, NJ (US);
Bradford J. Coale, Chester, NJ (US);
Jacob Macke, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 181 days.

(21) Appl. No.: 15/877,769

(22) Filed: Jan. 23, 2018

(65) Prior Publication Data

US 2018/0214192 A1  Aug. 2, 2018

Related U.S. Application Data (60) Provisional application No. 62/451,405, filed on Jan. 27, 2017.

(51) Int. Cl.
*A61B 17/86* (2006.01)
*A61L 31/14* (2006.01)
*A61L 31/02* (2006.01)
*A61B 17/00* (2006.01)

(52) U.S. Cl.
CPC .......... *A61B 17/866* (2013.01); *A61B 17/863* (2013.01); *A61B 17/8645* (2013.01); *A61L 31/022* (2013.01); *A61L 31/146* (2013.01); *A61B 17/8605* (2013.01); *A61B 17/8625* (2013.01); *A61B 17/8685* (2013.01); *A61B 2017/00526* (2013.01); *A61L 2430/02* (2013.01)

(58) Field of Classification Search
CPC .............. A61B 17/866; A61B 17/8645; A61B 17/3431
See application file for complete search history.

(56) References Cited

U.S. PATENT DOCUMENTS

| | | | |
|---|---|---|---|
| 4,272,855 A | 6/1981 | Frey | |
| 5,098,434 A | 3/1992 | Serbousek | |
| 5,360,448 A * | 11/1994 | Thramann | A61B 17/863 606/60 |
| 6,030,162 A * | 2/2000 | Huebner | A61B 17/1682 411/263 |

(Continued)

FOREIGN PATENT DOCUMENTS

WO  2018140375 A1  8/2018

OTHER PUBLICATIONS

"International Application Serial No. PCT US2018 014776, International Search Report dated Jun. 7, 2018", 6 pgs.

(Continued)

*Primary Examiner* — Christian A Sevilla
(74) *Attorney, Agent, or Firm* — Schwegman Lundberg & Woessner, P.A.

(57) ABSTRACT

Various different porous screws and pegs are disclosed herein, as are methods of manufacturing such porous pegs or screws. The porous screws and pegs, in certain examples, are formed through additive manufacturing and have improved porosity for bone ingrowth. In certain cases, additive manufacturing or another manufacturing technique can be used to cover only part or all of the threads of the screws or pegs disclosed herein with a porous material. Such screws or pegs can have porosity but also threads that are capable of effectively digging into bone.

20 Claims, 9 Drawing Sheets

(56) References Cited

U.S. PATENT DOCUMENTS

| | | | |
|---|---|---|---|
| 6,139,550 A | 10/2000 | Michelson | |
| 7,272,855 B1 | 9/2007 | Yemeni et al. | |
| 8,496,710 B2 | 7/2013 | Bagga et al. | |
| 8,979,911 B2 | 3/2015 | Martineau et al. | |
| 2006/0276788 A1* | 12/2006 | Berry | A61B 17/7005 606/286 |
| 2007/0225785 A1 | 9/2007 | Park | |
| 2009/0326671 A1 | 12/2009 | Schofield | |
| 2010/0042215 A1* | 2/2010 | Stalcup | A61B 17/68 623/16.11 |
| 2010/0298950 A1 | 11/2010 | Mcdonnell et al. | |
| 2011/0264151 A1* | 10/2011 | Davis | A61B 17/7035 606/305 |
| 2012/0277804 A1* | 11/2012 | Bhatnagar | A61B 17/7208 606/298 |
| 2012/0277869 A1 | 11/2012 | Siccardi et al. | |
| 2013/0056912 A1 | 3/2013 | O'neill et al. | |
| 2016/0157908 A1* | 6/2016 | Cawley | B22F 3/1055 606/301 |

OTHER PUBLICATIONS

"International Application Serial No. PCT US2018 014776, Written Opinion dated Jun. 7, 2018", 9 pgs.

"Zimmer Trabecular Metal Osteonecrosis Intervention Implant: Surgical Technique", [Online]. Retrieved from the Internet: <URL: http://www.rpa.spot.pt/getdoc/170401d7-f871-4d88-8e09-aee3e3178cd7/On_rod.aspx>, (2005), 4 pgs.

"International Application Serial No. PCT US2018 014776, Invitation to Pay Add'l Fees and Partial Search Rpt dated Apr. 9, 2018", 11 pgs.

* cited by examiner

POROUS FIXATION DEVICES AND METHODS

PRIORITY APPLICATIONS

This application claims the benefit of priority to U.S. Provisional Patent Application Ser. No. 62/451,405, filed Jan. 27, 2017, the content of which is incorporated herein by reference in its entirety.

FIELD OF THE DISCLOSURE

The present disclosure relates to surgical implant systems, including implants, instruments, and methods for installing an implant. Specifically, the present disclosure relates to porous screws and pegs, and methods of manufacturing and/or implanting the porous screws and pegs.

BACKGROUND

Bone screws are used in various orthopedic surgical contexts to provide stability and fixation to the biological tissue. For example, bone screws are used in trauma applications, in joint replacements, or in bone plating applications. A primary concern with bone screws is to ensure that the screw adequately fixes to bone and does not back out of the bone during the life cycle of that device. Including porosity in certain areas of the screw can augment the fixation of the screw, particularly given variation in bone quality and properties. Existing screws suffer in one (1) or more of these areas, for example the screws might be susceptible to backing out and/or have poor bone fixation.

The present disclosure provides bone screws and pegs that improve on existing bone screws and pegs.

SUMMARY

To better illustrate the systems disclosed herein, a non-limiting list of examples is provided here:

Example 1 includes a bone screw comprising a shaft having a thread, the thread, having a thread core formed of a first biocompatible material, wherein the thread defines a root and a crest, a proximal thread face is disposed between the root and the crest on a first side of the thread, and a distal thread face is disposed between the root and the crest on a second side of the thread. A porous layer of a second biocompatible material can cover only part of the proximal or distal thread face of the thread.

In Example 2, the first biocompatible material of the bone screw of Example 1 can optionally be a non-porous metal or metal alloy, and the thread core can be formed entirely of the first biocompatible material.

In Example 3, the interstitial spaces can be formed between adjacent crests of the thread and at leak some of the interstitial spaces can include a porous layer of the second biocompatible material.

Example 4 includes a bone screw comprising a core formed of a first biocompatible material, the core having a distal threaded section, an intermediate section, and a proximal head section, and a porous sleeve covering the intermediate section of the core, the porous sleeve being composed of a second biocompatible material that has a porous architecture that replicates natural cancellous bone.

In Example 5, the first biocompatible material of the bone screw of Example 4 can be a non-porous metal or metal alloy, or a metal or metal alloy with a porosity that is lower than a porosity of the porous sleeve.

In Example 6, the proximal head section of the bone screw of Example 4 can define a first diameter, the intermediate section can define a second diameter, and the distal threaded section can define a third diameter representing an outer diameter of the threads in the distal threaded section, and the second diameter can be smaller than the first and third diameters.

Example 7 includes a method of manufacturing a bone screw comprising forming a core having a section with a thread via additive manufacturing, the core being composed of a first biocompatible material, wherein the thread defines a root and a crest, a proximal thread face is disposed between the root and the crest on a first side of the thread, and a distal thread face is disposed between the root and the crest on a second side of the thread. The method further comprises covering only part of the proximal or distal thread face, by way of additive manufacturing, with a porous layer of a second biocompatible material.

In Example 8, the second biocompatible material of the bone screw of Example 7 can have a porous architecture that replicates natural cancellous bone.

In Example 9, the core of the bone screw of Examples 7-8 can define interstitial spaces between adjacent crests of the thread, and the method further comprises covering part of a first of the interstitial spaces with a porous layer of the second biocompatible material using additive manufacturing.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

In describing the examples of the disclosure illustrated and to be described with respect to the drawings, specific terminology will be used for the sake of clarity. However, the examples are not intended to be limited to any specific terms used herein, and it is to be understood that each specific term includes all technical equivalents.

Various porous fixation devices, such as porous screws and pegs, are disclosed herein. The porous screws and pegs, in some cases, can be formed through additive manufacturing techniques, such that porosity can be embedded on and/or intermeshed with threading on the screw or peg. In an example, porosity can be formed on the threads of the screw or peg themselves and/or on other portions of the screw or peg. The screws or pegs can be used in various contexts, in an example for fixation of a portion of a joint prosthesis to bone, fixation of plating to bone, or in trauma applications.

Figure 1A:
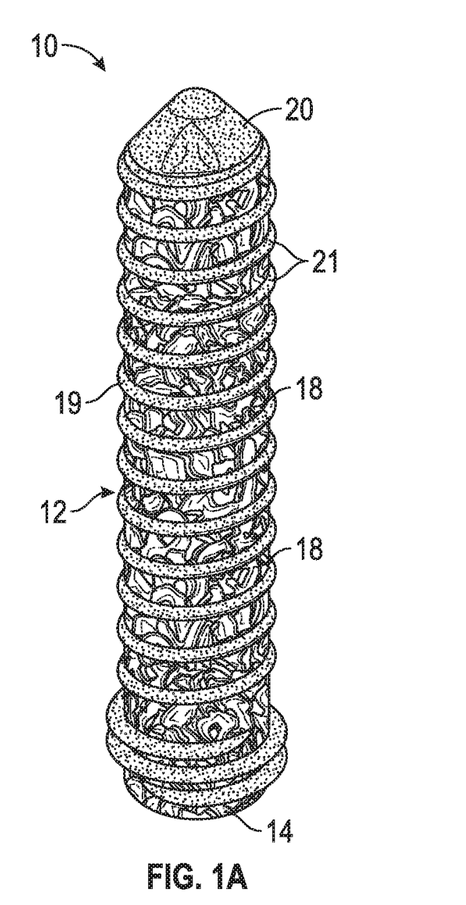
FIGS. 1A-B are side and top perspective views of a porous screw according to an example of the disclosure.
Figure 1B:
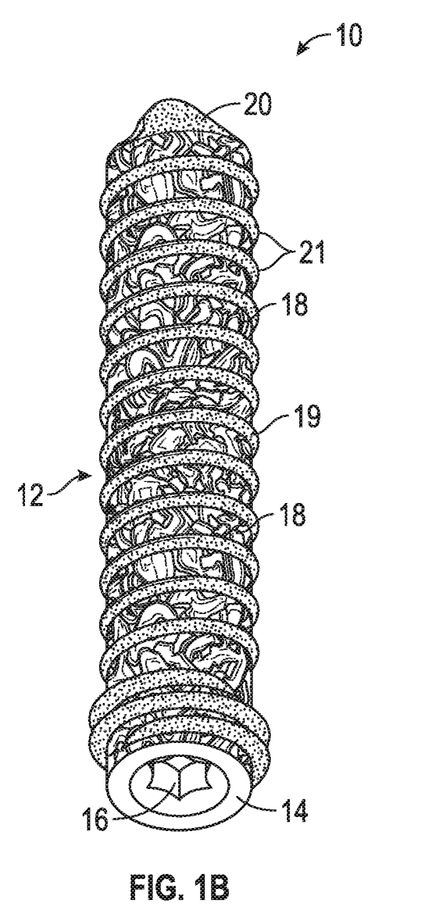

Referring to FIGS. 1A-B, an example of a porous screw 10 is disclosed. Porous screw 10 can include a shaft 12 that is threaded along part or all of its length and a head 14. Head 14 can include threads, in an example for interacting with a threaded hole in a bone plate, joint replacement, or other prosthesis. Alternatively, head 14 can be non-threaded or smooth or have threads for engaging bone instead of a prosthesis. Head 14 can further include a drive engagement 16, for instance a hexagonal-shaped recess configured to engage with a hexagonal-shaped male portion of a driving instrument (not shown). Drive engagement 16 can take any shape (e.g., triangular, oval, diamond, square, hexagonal, etc.) and/or have internal threading or press-fit features for engaging with the male part of the driving instrument. Screw 10 can also have a distal tip 20 forming a point for insertion into bone, which in an example can include self-tapping features (not shown), such as a cutting flute(s). The cutting flute(s) would allow screw 10 to self-drill into bone and might not require a pre-tapping operation to be performed for insertion of screw 10 into bone.

The entirety of screw 10 can be formed through an additive manufacturing process, such as 3D printing, selective laser sintering, selective laser melting, or any other additive manufacturing process. As such, screw 10 can be manufactured with different materials at different regions and/or have porosity in certain regions, but not in others. For instance, shaft 12 can have a core that is formed of a first material by way of additive manufacturing, and outer surfaces of shaft 12 can be formed of a second material through the additive manufacturing process. The first material can be titanium or another suitable biocompatible metal or metal alloy (optionally non-porous), and the second material can be a porous material, such as OsseoTi®, which is commercially available from Biomet Manufacturing, LLC (Warsaw, Ind., USA). Thus, porous sections 18 can be formed over the core of shaft 12 through additive manufacturing. In an example, porous sections 18 can be formed of OsseoTi®. This can create a situation in which the core of screw 10 is a solid biocompatible metal or metal alloy, for example titanium, and outer surfaces of screw 10 include porous sections 18 that stimulate bone ingrowth when screw 10 is implanted in bone. In this and other examples, the core of screw 10 can be non-porous or it can have a porosity that is lower than the porosity of the outer surfaces of screw 10 formed of OsseoTi®. For instance, the porosity of the core can be approximately be anywhere between about zero to fifty percent (0-50%) porous. In addition, the core of shaft 12 can be formed with threading on the core, and then outer surfaces of shaft 12 can include OsseoTi® formed over part or all of the threading.

Figure 7A:
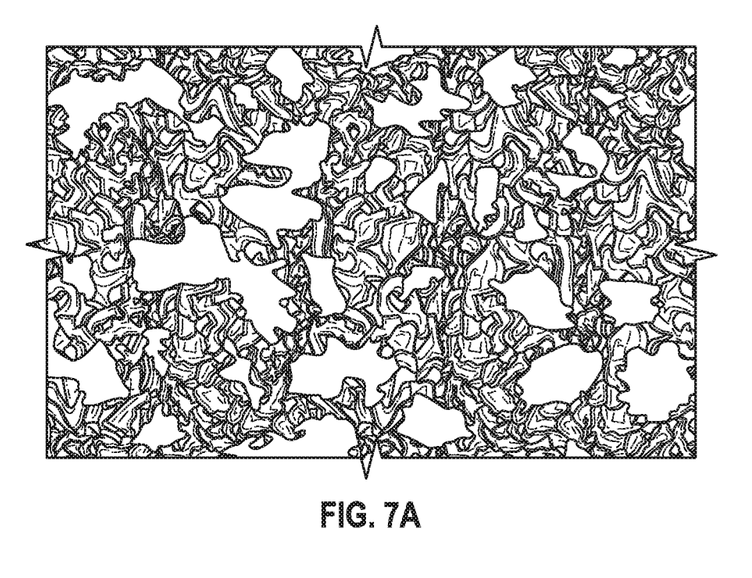
FIG. 7A illustrates OsseoTi®, a material that can be used to form any of the screws or pegs disclosed herein, as discussed in more detail below.
Figure 7B:
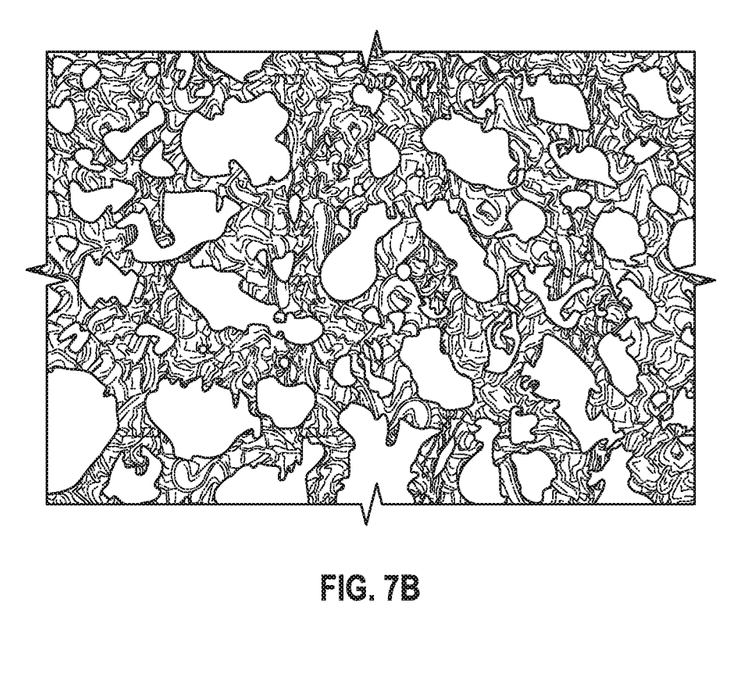
FIG. 7B illustrates human cancellous bone.

Briefly, OsseoTi® can be a titanium alloy, in an example Ti6Al4V, that is highly biocompatible, has high corrosion resistance, and includes a highly interconnected porous architecture that mimics the porous structure of human cancellous bone. FIGS. 7A-B illustrate the architecture of OsseoTi® as compared to human cancellous bone, and it is apparent that the architecture of OsseoTi® mimics that of cancellous bone. OsseoTi® can therefore enhance bone integration and ingrowth and can be used on select areas of screw 10 to improve osseointegration. In one exemplary implementation, the OsseoTi® porous metal construct can include a porosity of 70%.

Because screw 10 can be formed using an additive manufacturing process, the porosity present on screw 10 can be formed directly on the threads of shaft 12 themselves and/or on interstitial spaces 21 between the threads. In an example, using 3D printing or another additive manufacturing technique, the second material (e.g., OsseoTi®) can be deposited layer-by-layer on the core of screw 10, thereby attributing porosity to the thread surfaces themselves and/or interstitial spaces 21 between the threads. The core can also be formed through the same additive manufacturing technique, but using the first material detailed above (e.g., a non-porous metal or metal alloy, or a metal or metal alloy with a porosity that is lower than that of OsseoTi®). In an example, the porosity of the second material (e.g., OsseoTi®) can be anywhere between fifty to ninety-five percent (50-95%) porous.

In any of the prior examples of screw 10 or in any of the screws and/or pegs discussed below, when threads are described as themselves being formed of OsseoTi®, it can mean that the entire thread structure from root to crest (e.g., the entire thread depth) can be formed of OsseoTi®, or that a layer of OsseoTi® can be formed along part, substantially all, or an entirety of the surfaces defining the thread. In the latter case, the threads covered with a layer of OsseoTi® can be threading present on the core of shaft 12, which can be formed of a biocompatible metal or metal alloy (optionally non-porous), as discussed above.

More particularly, the threads of the above and below examples can be said to define a root, a crest, a proximal thread face between the root and crest on a first side of the thread, and a distal thread face between the root and the crest on a second side of the thread. Crest 19 is shown in FIGS. 1A-B, but the root and proximal/distal thread faces are hidden from view. In certain instances, a layer of OsseoTi® can be formed on part of the proximal and/or distal thread faces defining the thread, and a portion of the thread that is not formed of OsseoTi® can extend from the OsseoTi® layer. The protruding part can be crest 19 of the threads, which presents a sharp thread edge that can be formed from a non-porous biocompatible material (e.g., a non-porous metal or metal alloy) or a material that has a porosity that is lower than that of OsseoTi®. This results from the fact that the core of screw 10 can be formed of the first biocompatible material discussed above, with threading, and the core can then be covered via additive manufacturing with OsseoTi®. Since in an example only part of the proximal and/or distal thread faces are covered with OsseoTi®, a portion of the core of screw 10 that defines crest 19 of the thread can protrude from or beyond the OsseoTi® layer. This creates a situation in which a non-porous, sharp crest 19 can be presented at the outermost parts of the threads for digging into bone. In addition, porous OsseoTi® can be formed on non-crest areas of the threads and/or at interstitial spaces 21 to facilitate bone ingrowth into screw 10 at the same time.

OsseoTi® can cover roughly ten percent to about ninety percent (10-90%) of the proximal and/or distal thread faces of each thread, or it can cover anywhere between about thirty percent to about sixty percent (30-60%) of the proximal and/or distal thread faces. Thus, as noted above, crest 19 of the threads can be somewhat exposed and define a sharp edge formed of the material of the core of shaft 12, which in an example is the first biocompatible material discussed above. Crests 19 can therefore each present a sharp, non-porous edge that is more suited to dig into bone than an ill-defined porous edge.

In the above examples, it can be said that each thread can have a thread core formed of a non-OsseoTi® material (e.g., a non-porous metal or metal alloy) and a layer of OsseoTi® can cover part or all of the thread core to establish a porous layer covering part or all of the thread. In certain instances, interstitial spaces 21 can also include a porous material (e.g., OsseoTi®) that covers part or all of each interstitial space 21. For instance, the core of shaft 12 and the threads thereof can be formed through additive manufacturing out of a first biocompatible material (e.g., a non-porous metal or metal alloy), and porous OsseoTi® can be deposited in interstitial spaces 21 to cover part or all of spaces 21. The OsseoTi® can have a thickness that is anywhere between about ten percent to about ninety percent (10-90%) of the depth of adjacent threads bordering the particular interstitial space 21, or it can have a thickness that is anywhere between about thirty percent to about sixty percent (30-60%) of the depth of the adjacent threads. If only part of an interstitial space 21 is covered, the remaining areas can be exposed parts of the core of shaft 12, which can be formed of the first biocompatible material.

In yet another example, the thread can itself include a thread core formed of the first material discussed above (e.g., a non-porous metal or metal alloy) and alternating layers of a porous material (e.g., OsseoTi®) can be formed on the proximal and/or distal thread faces of the thread, such that the thread core is exposed between layers of the porous material. In addition, interstitial spaces 21 between the threads in any of the above examples can include a porous material (e.g., OsseoTi®) or another material (e.g., a non-porous metal or metal alloy). Thus, many combinations are possible and are envisioned by the present disclosure and are applicable to any of the examples discussed above and/or below with reference to the figures or otherwise.

In even further examples, it is contemplated that porosity can vary or be uniform along the length of shaft 12 of screw 10. The porosity could for instance be greater at a distal section of shaft 12 as compared to the porosity at an intermediate and/or a proximal section of shaft 12, or vice versa. Porous OsseoTi® can also be present along only part of the threads and/or interstitial spaces 21 of shaft 12 while not being present on other areas of shaft 12. For instance, OsseoTi® might be present only on the threads and/or interstitial spaces 21 of a distal section of shaft 12, an intermediate section of shaft 12, a proximal section of shaft 12, or any combination of the foregoing sections. The other sections not utilizing OsseoTi® might have traditional non-porous threads in these examples. Indeed, the non-porous threads can be formed by the core of screw 10 (e.g., a non-porous metal or metal alloy).

The depicted embodiment in FIGS. 1A-B includes threading along substantially the entire length of shaft 12, but in alternate examples only part of shaft 12 is threaded while other parts are non-threaded or smooth. For instance, a proximal section of shaft 12 can include threading that is non-porous (e.g., a non-porous metal or metal alloy) or porous (e.g., OsseoTi®), an intermediate section of shaft 12 can be non-threaded and/or smooth, and a distal section of screw 10 can include threading that is non-porous (e.g., a non-porous metal or metal alloy) or porous (e.g., OsseoTi®), in any combination. As contemplated above, interstitial spaces 21 between the threads in the proximal and/or distal sections can also include porosity (e.g., be formed of OsseoTi®). In a further example (discussed in more detail below with reference to pegs 110, 210, 310), the intermediate section of screw 10 can be formed of a porous material (e.g., OsseoTi®) and have a design similar to shafts 112, 212, 312. It is also contemplated that screw 10 can be cannulated through its entire length so that a K-wire can be received in shaft 12.

Further, the threads in the proximal and distal sections of shaft 12 can have different pitches. For example, the threads in the proximal section can have a finer pitch than threads in the distal section of screw 10. This can enable screw 10 to be used as a compression screw in, for instance, fracture applications.

In another example, screw 10 can have threads along the length of its shaft 12, but the pitch of the threads can be variable instead of constant (the depicted example of FIGS. 1A-B have constant-pitch threads). For instance, shaft 12 can have a continuous thread with a pitch that changes from a coarser pitch near a distal section of shaft 12 to a finer pitch near a proximal section of shaft 12. Such a variable pitch screw 10 can also be used in compression-type applications to compress bone parts together. In an alternate example, the variable pitch continuous thread can have a finer pitch near the distal section of shaft 12 changing to a coarser pitch near the proximal section of shaft 12. Further, the variable pitch continuous thread can also extend along only part of shaft 12 instead of the entire length of shaft 12, as discussed above.

Screw 10 can further include a root diameter for shaft 12 that is tapered from tip 20 to adjacent head 14, or it can include a constant-diameter root. FIGS. 1A-B show screw 10 with a constant-diameter root for shaft 12, except at tip 20 of course. In addition, in these and other examples, an outer diameter of the threads on shaft 12 can be constant along part or all of shaft 12, or alternatively variable (e.g., tapered). In an example, an outer diameter of the threads can be tapered in a proximal section, intermediate section, and/or distal section of shaft 12. Further, the screw threads on shaft 12 can be cortical threads, cancellous threads, or some combination of both to suit the application at hand. Cortical threads are characterized by a pitch that is finer than that of cancellous threads, which are coarser. Cortical threads with their finer pitch are more suited to dig into cortical bone, while cancellous threads with their coarser pitch are more suited to dig into cancellous bone. In an example, screw 10 can include cancellous threads at a distal section of shaft 12 and cortical threads at a proximal section of shaft 12 and/or on head 14 to engage with cortical bone.

After forming screw 10 through additive manufacturing, screw 10 can undergo post-processing. As an example, screw 10 can be subject to heat treating, machining, electrical discharge machining (EDM) processes, or other post-processing techniques. Such post-processing can improve thread sharpness for the threads on shaft 12, form self-tapping features on the threads, and/or improve drive engagement 16. At non-porous parts of screw 10. Screw 10 can also be polished, bead blasted, or undergo other post-processing as well. It has been found, however, that such techniques can be, but not necessarily are, unsuitable for post-processing porous sections 18 of screw 10.

FIGS. 2A-4B illustrate various embodiments of porous pegs 110, 210, 310. Each of porous pegs 110, 210, 310 can include a porous shaft 112, 212, 312 and a non-porous core 111, 211, 311. As with screw 10, pegs 110, 210, 310 can be formed using any of the aforementioned additive manufacturing techniques, and cores 111, 211, 311 and shafts 112, 212, 312 can be formed from any of the first and second materials discussed above. As an example, cores 111, 211, 311 can be formed of a non-porous metal or metal alloy (e.g., titanium), and shafts 112, 212, 312 can be formed using additive manufacturing from OsseoTi®. Thus, shafts 112, 212, 312 can facilitate positive bone in growth via the use of OsseoTi® when pegs 110, 210, 310 are implanted in bone. Each of pegs 110, 210, 310 can further include a head 114, 214, 314 that has a drive engagement 116, 216, 316. Drive engagements 116, 216, 316 can take the form of any of the aforementioned disclosed drive engagements 16 for screw 10.

Figure 2A:
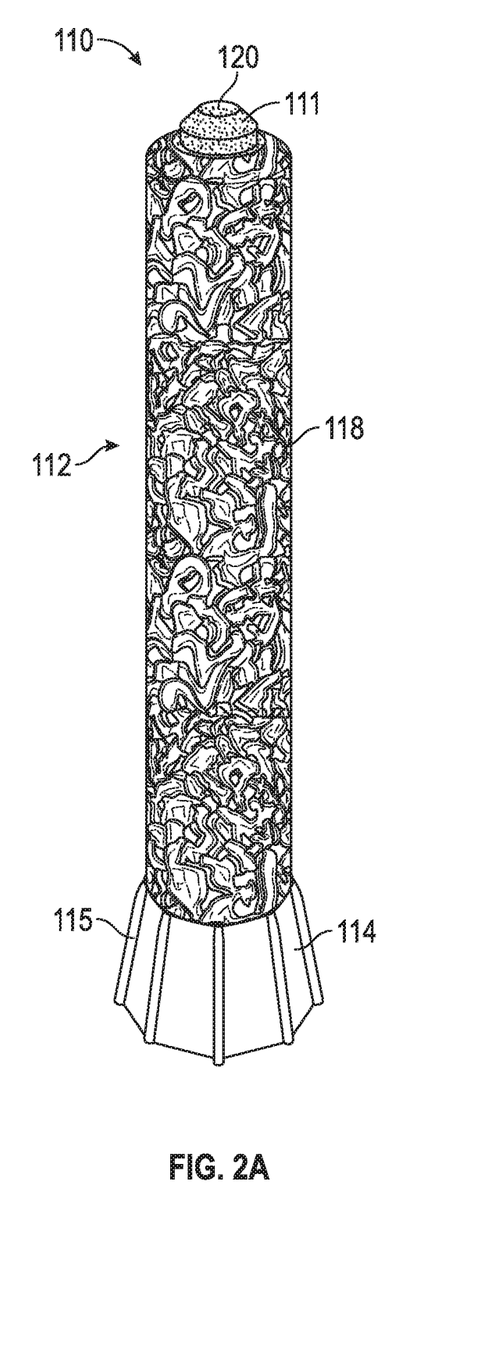
FIGS. 2A-B are side and top perspective views of a first porous peg according to an example of the disclosure.
Figure 2B:
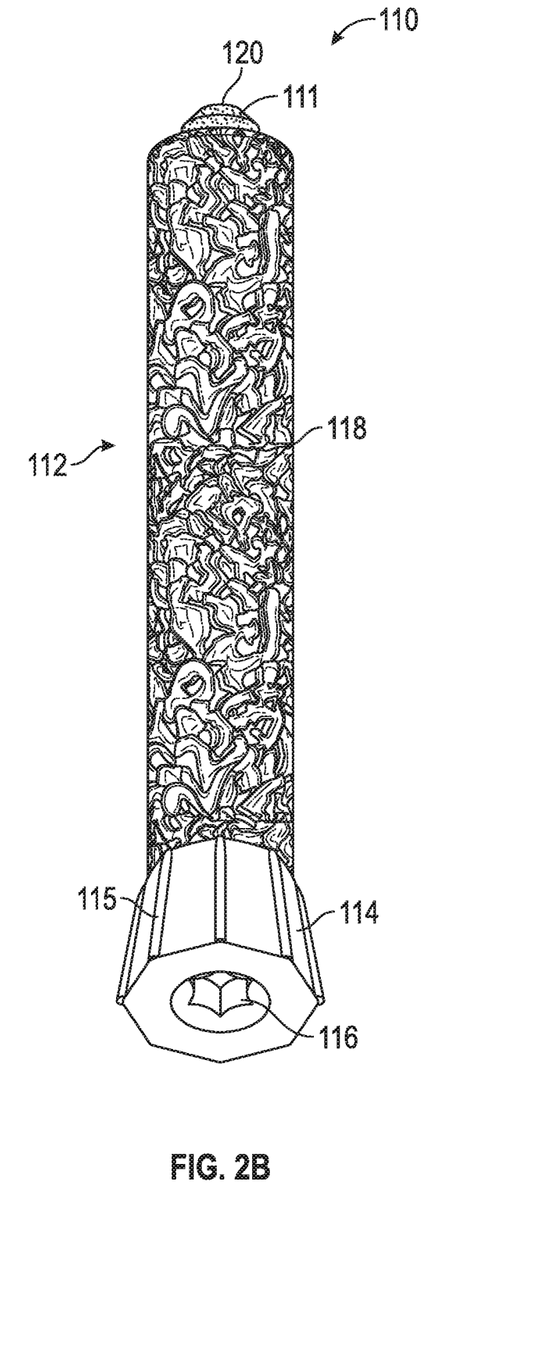

Referring to FIGS. 2A-B, peg 110 can include a shaft 112 that is non-threaded along its entire length and is partially or substantially entirely formed of OsseoTi®. In an example, shaft 112 can have a substantially constant diameter along a majority of its length, or substantially all of its length, and a tapered tip 120. Core 111 can, in some cases, protrude slightly from the OsseoTi® of shaft 112 at tip 120, as shown. In an example, head 114 of peg 110 can also be tapered and can include one (1) or more protruding ribs 115. Ribs 115 can extend axially along part or substantially all of head 114 so as to substantially coincide with a longitudinal axis of shaft 112.

Figure 3A:
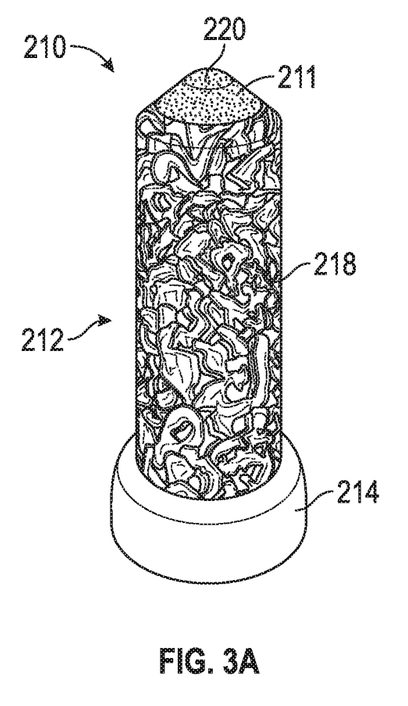
FIGS. 3A-B are side and top perspective views of a second porous peg according to another example of the disclosure.
Figure 3B:
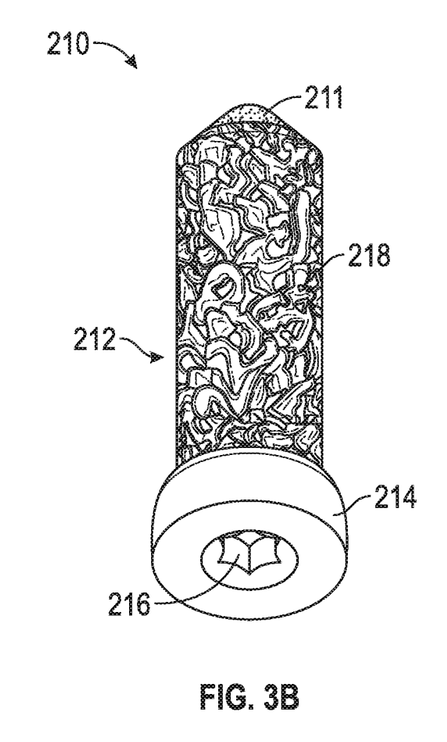

Peg 210, as shown in FIGS. 3A-B, is similar to peg 110 but can instead include a head 214 that is smooth and/or forms a rounded shape. Like peg 110, peg 210 can have a shaft 212 with a substantially constant diameter along a majority or substantially all of its length and a tapered tip 220. In addition, core 211 can also protrude slightly from the OsseoTi® of shaft 212 at tip 220, as shown.

Figure 4A:
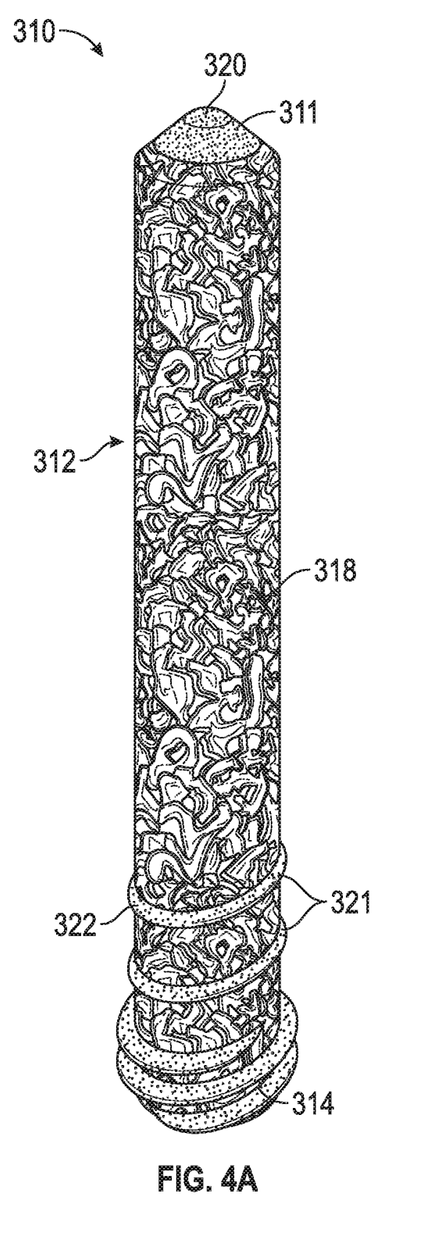
FIGS. 4A-B are side and top perspective views of a third porous peg according to yet another example of the disclosure.
Figure 4B:
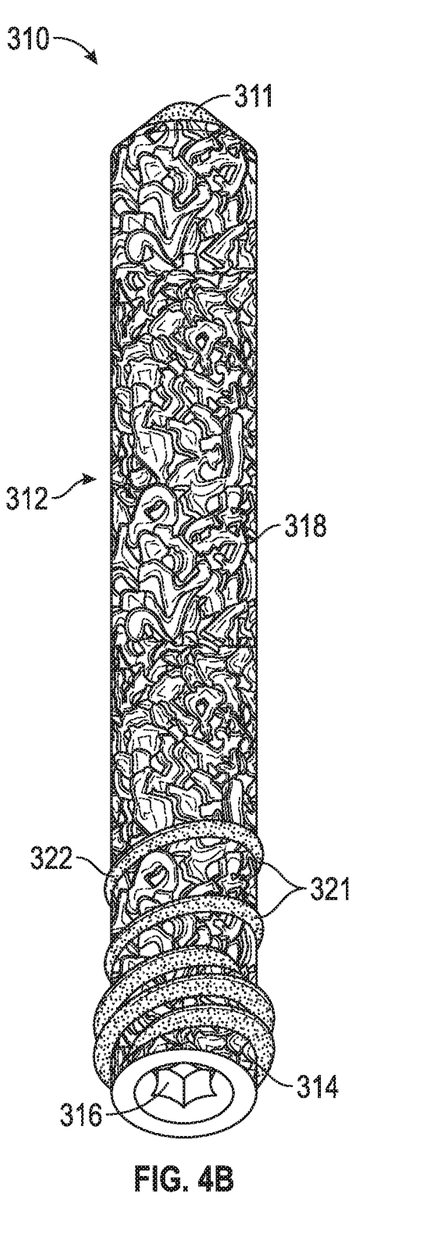

Peg 310 is illustrated in FIGS. 4A-B. Peg 310 can include a head 314 that is threaded for engagement with a threaded hole (e.g., in a bone plate, joint prosthesis, or other prosthetic component) or bone. In addition, shaft 312 of peg 310 can include one (1) or more threads 322, in an example, for engaging bone when peg 310 is inserted into bone. As shown, and similar to screw 10, because peg 310 is formed by way of an additive manufacturing process, threads 322 themselves can include porosity as threads 322 themselves can be formed from OsseoTi®, which replicates the architecture of natural cancellous bone. In addition, like screw 10, interstitial spaces 321 on shaft 312 between threads 322 can be formed from OsseoTi® and therefore include the porosity and attributes of that material, as described in detail above. As with screw 10, peg 310 can also be subject to post processing in the manner described above (e.g., particularly as to threads 322, which can be machined, sharpened, and/or include self-tapping features).

Alternative examples of screw 10 (not shown) can also be provided that incorporate features of pegs 110, 210, and/or 310. For instance, screw 10 can have threads along part of shaft 12, non-threaded OsseoTi® sections along other parts of shaft 12. (e.g., as with shafts 112, 212, 312 of pegs 110, 210, 310), and/or further threads formed on shaft 12 that provide boundaries for the non-threaded OsseoTi® sections. In an example, an intermediate section of shaft 12 can include a non-threaded OsseoTi® section similar to pegs 110, 210, 310, while a proximal and/or distal section of shaft 12 can include threads, similar to those shown in FIGS. 1A-B. Alternatively, a non-threaded OsseoTi® section can be positioned at a proximal section of screw 10 immediately adjacent head 14, and a remainder of shaft 12 can be threaded similar to as shown in FIGS. 1A-B, Even further, a proximal and intermediate section of shaft 12 can be threaded similar to as shown in FIGS. 1A-B, while a distal section of shaft 12 can include a non-threaded OsseoTi® section similar to shafts 112, 212, 312. In another example, non-threaded. OsseoTi® sections and threaded sections can alternate along shaft 12, such that a non-threaded OsseoTi® section is between two (2) threaded sections and a threaded section is between two (2) non-threaded OsseoTi® sections. As such, any combination of threaded sections and non-threaded OsseoTi® sections that are similar to those of pegs 110, 210, 310 can be utilized along shaft 12 to create an alternate screw 10 with improved fixation characteristics. It should be noted that although threaded sections are not described above as OsseoTi® sections, such threaded sections can be formed of OsseoTi® as described in connection with screw 10. Alternatively, in another example, the threaded sections can be formed of a non-porous biocompatible metal or metal alloy (e.g., titanium), and/or certain threaded sections can be formed of OsseoTi® while other threaded sections are formed of a non-porous biocompatible metal or metal alloy.

Another example of a porous screw 410 is shown in FIGS. 5A-F. Similar to porous screw 10, porous screw 410 can be formed by way of any of the additive manufacturing techniques disclosed above. Thus, it is to be understood that the different components of porous screw 410 discussed below can all be formed through additive manufacturing.

Porous screw 410 can include a shaft 412 and a head 414 with a drive engagement 416. In an example, head 414 can be integral or monolithic with shaft 412 by virtue of forming shaft 412 and head 414 through an additive manufacturing process. Shaft 412 can have a distal threaded section 430 leading to a tip 432 that forms a point. As shown in FIGS. 5C and 5F, tip 432 can have one (1) or more cutting flutes 434 configured to cut into bone as screw 410 is screwed into bone, for example two (2) cutting flutes 434. In an example, flutes 434 can form self-tapping features on screw 410. Cutting flutes 434 can be disposed on opposite sides of shaft 412 of screw 410. As shown in FIG. 5D, the threads of threaded section 430 can also be defined by a lower angled thread face 431 and an upper substantially-perpendicular or alternatively substantially-transverse thread face 429. In an example, an angle between faces 429, 439 can be approximately thirty two degrees (32°) plus/minus two and a half degrees (+/−2.5°). Further, in another example, the pitch of the threads in threaded section 430 can be constant or variable. For instance, the pitch could vary from a greater pitch near tip 432 to a smaller pitch as one approaches a proximal part of threaded section 430. This could have the effect of creating compression between bone parts as screw 410 is screwed into bone.

Figure 5A:
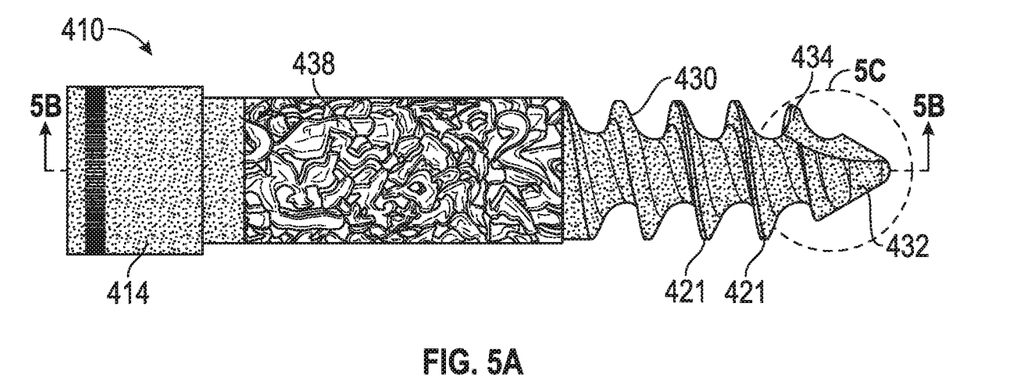
FIG. 5A is a side view of a porous screw according to an example of the disclosure.
Figure 5B:
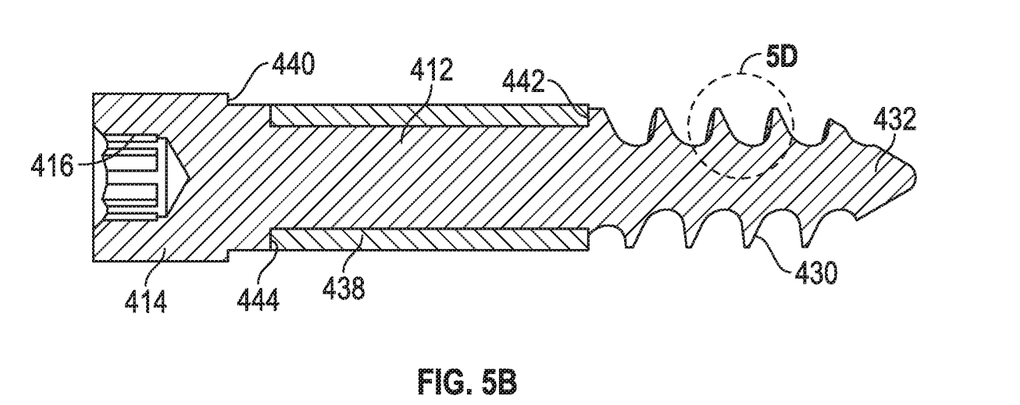
FIG. 5B is a cross-sectional view of the porous screw of FIG. 5A.
Figure 5C:
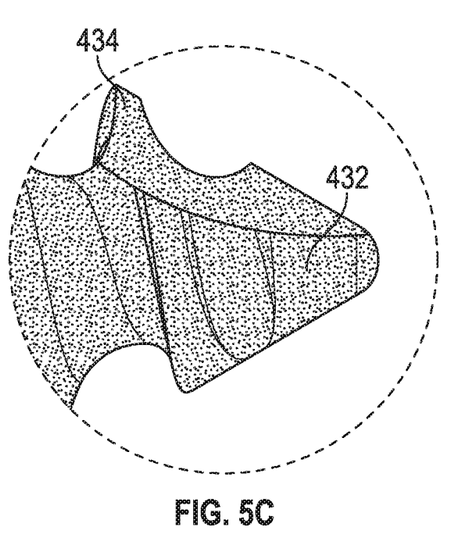
FIGS. 5C-F are close-up detailed views of a distal section (FIG. 5C, 5F), threads (FIG. 5D), and a head (FIG. 5E) of the porous screw of FIG. 5A.
Figure 5D:
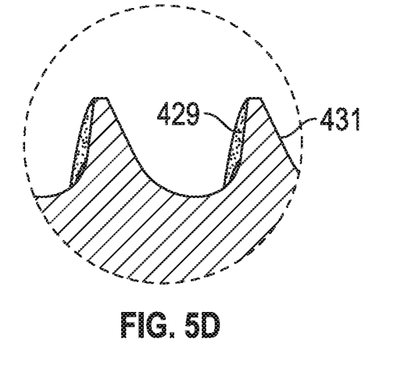
Figure 5E:
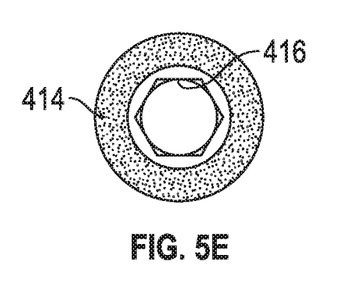
Figure 5F:
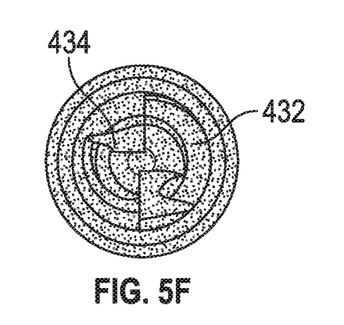

A sleeve 438 can be formed over a portion of shaft 412, as shown in FIGS. 5A-B. In an example, sleeve 438 can be formed using OsseoTi® and have the porous structure of OsseoTi® material, as described above. By contrast, in an example shaft 412 and head 414 can be formed of a material that is different from OsseoTi®. For instance, shaft 412 and head 414 can be formed of a non-porous metal or metal alloy as detailed above, or alternatively shaft 412 and head 414 can be formed of a porous metal or metal alloy having a different architecture and/or porosity from that of OsseoTi®. In yet another example, the threads on distal threaded section 430 can be formed of OsseoTi® in the manner set forth above for screw 10, such that the OsseoTi® porous architecture is embedded in and/or forms the threads of distal threaded section 430. In this example, an inner core of distal threaded section 430 can be formed of a non-porous material (e.g., a non-porous metal or metal alloy), while the threads and/or interstitial spaces 421 between the threads can be formed using OsseoTi® so as to have an architecture that replicates cancellous bone. Thus, distal threaded section 430 and/or interstitial spaces 421 can utilize the OsseoTi® features of the numerous examples discussed above with reference to screw 10.

Sleeve 438 can be retained between a portion of a thread on distal threaded section 430 and head 414, as shown in FIG. 5B. In particular, a proximal-most thread of distal threaded section 430 can form a step 442, and a step 444 can be formed adjacent head 414. A distance between steps 442, 444 can be approximately the same as a length of sleeve 438 and can contact end portions of sleeve 438 so as to retain sleeve 428 longitudinally. In another example, the distance between steps 442, 444 can be slightly larger or smaller than the length of sleeve 438. If the distance is larger than sleeve 438, sleeve 438 can be formed on shaft 412 so that a slight amount of movement therebetween is permitted (e.g., when screw 410 is loaded). In another example, sleeve 438 is fixed relative to shaft 412 so that substantially no movement occurs therebetween when screw 410 is loaded. As stated previously, sleeve 438 can be formed of OsseoTi® that is deposited on shaft 412 through an additive manufacturing process. By virtue of the fact that additive manufacturing is used, shaft 412 and head 414 can also form an integral or monolithic structure and still an intermediate portion of shaft 412 can fit within sleeve 438.

Head 414 of screw 410 also can include a step 440, such that head 414 is enlarged and/or has a diameter that is larger than a diameter of shaft 412. As explained in the context of a surgical method below, step 440 can be used to engage with a portion of a hole in a prosthetic device (e.g., another step in the hole) so that screw 410 can be used to fix the prosthetic device to bone. In an example, the hole in the prosthetic device can be countersunk in the prosthetic device (e.g., bone plate, joint component, etc.), such that head 414 can fit in the countersink and step 440 can contact a step in the hole and enable screw 410 to fix the prosthetic device to bone. Drive engagement 416 of screw 410 can also be any of the drive engagements discussed previously, as an example a hexagonal-shaped recess (shown in FIG. 5E), triangular, oval, square, or any other shape allowing non-rotational engagement with a male part of a driving instrument.

Figure 6A:
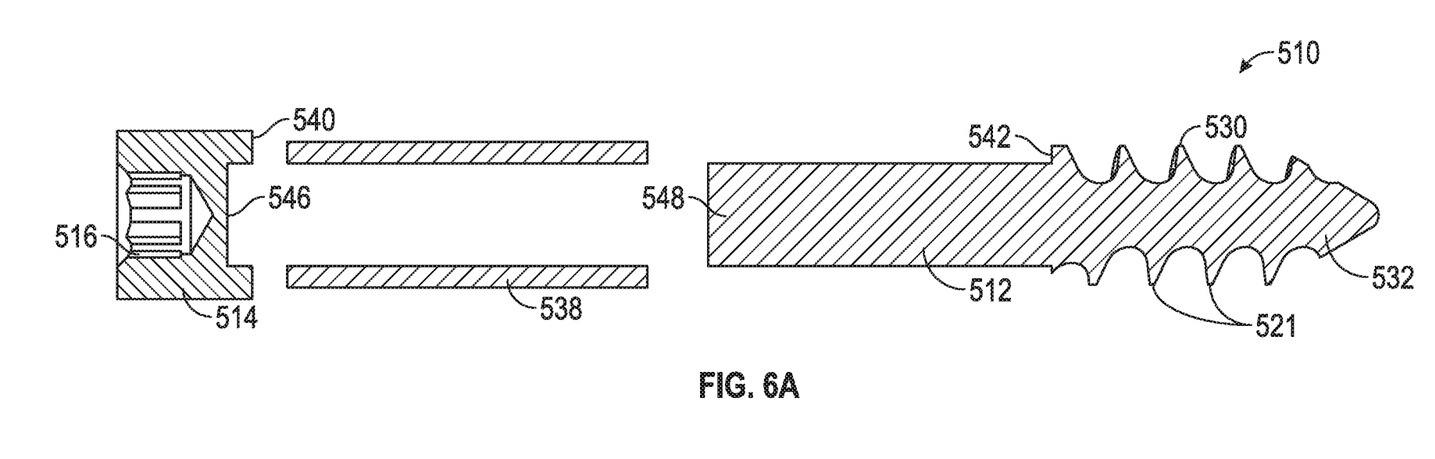
FIGS. 6A-B are cross-sectional views of an alternative example of the porous screw of FIG. 5A.
Figure 6B:
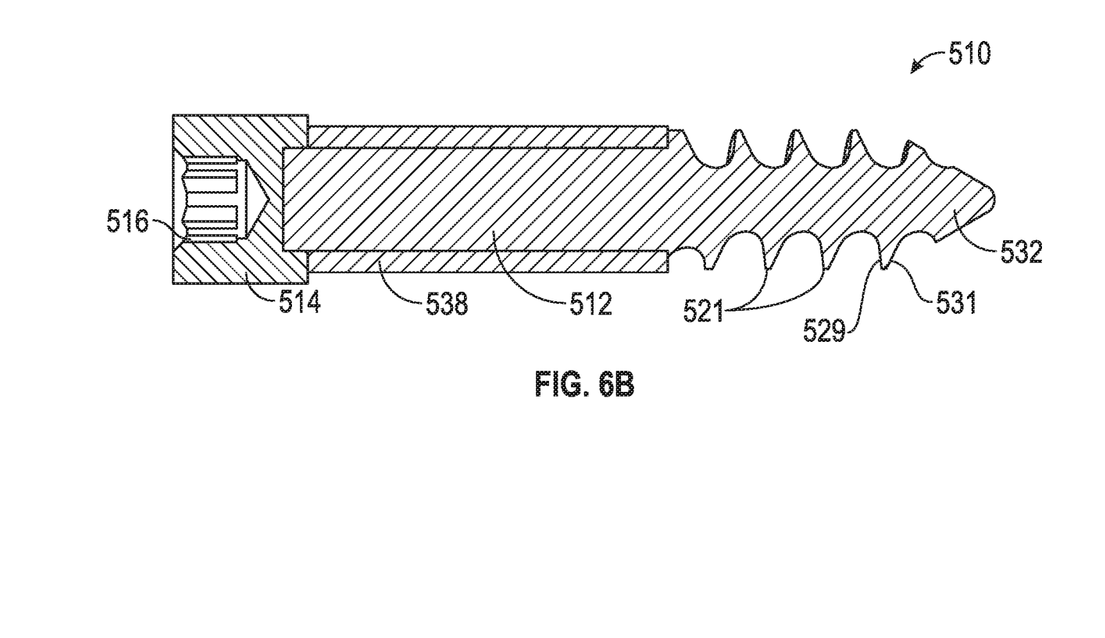

An alternate example of screw 410—screw 510—is shown in FIGS. 6A-B. As with prior examples of the disclosure, like reference numerals refer to like elements in this example and, predominantly, only the differences between screws 410, 510 will be discussed. In this example, some or all of the components of screw 510 may be formed by traditional manufacturing techniques and not additive manufacturing, although as discussed below some alternate examples can provide for the use of additive manufacturing of certain components.

As shown in FIG. 6B, screw 510 can include a separate head 514 and shaft 512 structure. Head 514 can have a recess 546 that can be cylindrical, hexagonal, square, or another shape, which can mate with a projecting part 548 of shaft 512. A fixed connection can be established between recess 546 and projecting part 548 as, for example, by laser welding, press fitting, a threaded (e.g., screw and nut) engagement, or any other fixed engagement. In addition, the engagement can be non-rotational, such that head 514 is non-rotationally fixed relative to shaft 512. In an example, head 514 and/or shaft 512 can be produced through traditional manufacturing techniques and not through additive manufacturing. Further, head 514 and/or shaft 512 can also be formed of a non-porous material (e.g., a non-porous metal or metal alloy), or a material that has a porosity that is less than that of OsseoTi®. In an alternate example, however, head 514 and/or shaft 512 can be produced through additive manufacturing using the materials and/or having any of the material attributes discussed above with reference to screw 410. As an example, shaft 512 can be formed via additive manufacturing and/or from different materials with different porosities, or can be produced via additive manufacturing and be a non-porous single material (e.g., a biocompatible metal or metal alloy). If porosity is desired, for example, shaft 512 can utilize additive manufacturing to form a non-porous core of a first material (e.g., a metal or metal alloy) and a porous distal threaded section 530. In this example, OsseoTi® can be used to form outer layers of distal threaded section 530, and/or the threads themselves can be formed of OsseoTi®. Similar to screws 10, 410, interstitial spaces 511 can also be formed of OsseoTi®. Thus, distal threaded section 530 can be predominantly formed of OsseoTi®, to create porosity in that area and replicate the architecture of cancellous bone.

Screw 510 can also include a separate sleeve 538 that, in an example, is formed through traditional, non-additive manufacturing techniques. In an example, sleeve 538 is formed of a highly porous biornaterial useful as a bone substitute and/or cell and tissue receptive material. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is incorporated herein by reference. Other metals such as niobium, or alloys of tantalum and niobium with one another or with other metals may also be used.

Figure 8:
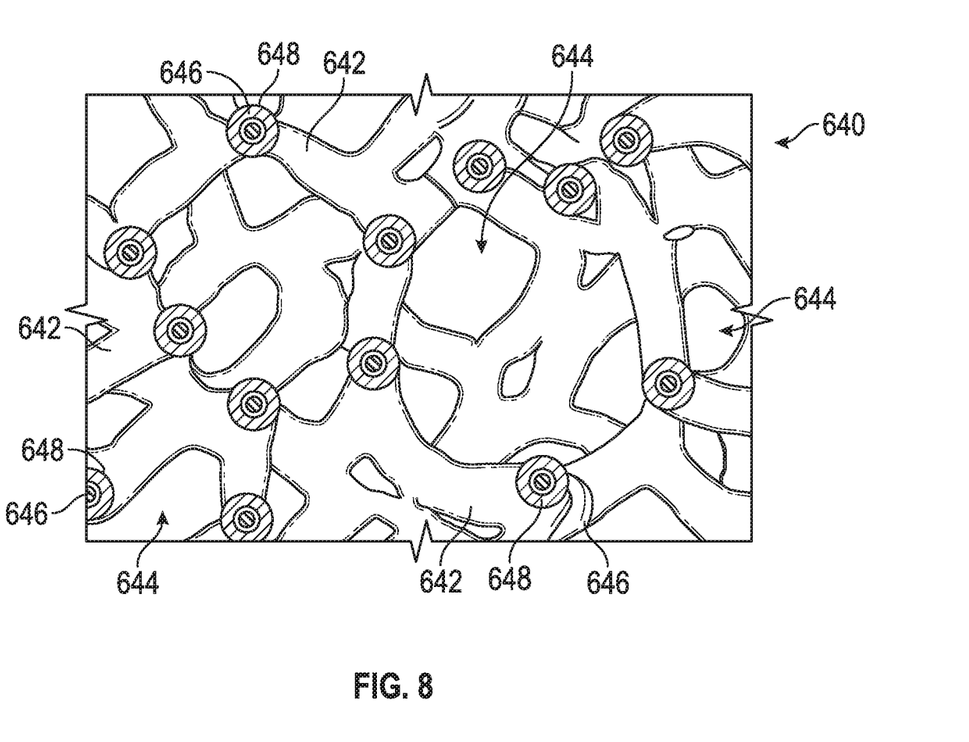
FIG. 8 illustrates the architecture of Trabecular Metal™, a material produced by Zimmer, Inc.

Generally, as shown in FIG. 8, porous tantalum structure 640 includes a large plurality of ligaments 642 defining open spaces 644 therebetween, with each ligament 642 generally including a carbon core 646 covered by a thin film of metal 648 such as tantalum, for example. The open spaces 644 between ligaments 642 form a matrix of continuous channels having no dead ends, such that growth of cancellous bone through porous tantalum structure 640 is uninhibited. The porous tantalum may include up to seventy-five to eighty-five percent (75-85%) or more void space therein. Thus, porous tantalum is a lightweight, strong porous structure which is substantially uniform and consistent in composition, and closely resembles the structure of natural cancellous bone, thereby providing a matrix into which cancellous bone may grow to anchor screw 510 into the surrounding bone of a patient.

Porous tantalum structure 640 may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization. This includes a gradation of pore size on a single implant such that pores are larger on a first end section to match cancellous bone and smaller on a second end section to match cortical bone, or even to receive soft tissue ingrowth. Such gradation of pore size can be applied to sleeve 538. Also, the porous tantalum could be made denser with fewer pores in areas of high mechanical stress. Instead of smaller pores in the tantalum, this can also be accomplished by filling all or some of the pores with a solid material which is described in further detail below.

The following is applicable to all examples set forth in the present disclosure where porosity is used on any of the disclosed screws or pegs. To provide additional initial mechanical strength and stability to the porous structure (e.g., OsseoTi® or Trabecular Metal™ portions of the disclosed screws or pegs), the porous structure may be infiltrated with filler material such as a non-resorbable polymer or a resorbable polymer. Examples of non-resorbable polymers for infiltration of the porous structure can include a polyaryl ether ketone (PAEK), such as polyether ketone ketone (PEKK), polyether ether ketone (PEEK), polyether ketone ether ketone ketone (PEKEKK), polymethylacrylate (PMMA), polyetherimide, polysulfone, and polyphenolsulfone.

Examples of resorbable polymers may include Polylactide (PLA), Polyglycolic acid (PGA), polylactic co-glycolic acid (PLGA), polyhydroxybutyrate (PHB), polyhydroxyvalerate (KW), Poly-L-lactide (PLLA), and copolymers thereof, polycaprolactone, polyanhydrides, and polywhoesters.

The pores of the porous parts disclosed herein may also be filled with other materials, such as bone growth proteins, antibiotics, or human derived, animal derived, or synthetic bone grafting materials. Each of the materials or combinations of any of these materials may provide a clinical advantage to the porous portion.

It should also be noted, for the screws and/or pegs of FIGS. 1A-4B, that instead of OsseoTi® being used as the applicable porous material, Trabecular Metal™ could be used. In these examples, the Trabecular Metal™ can be bonded, welded, and/or cold formed to the non-porous core of the screw and/or peg.

The screws and/or pegs disclosed herein can be used in various orthopedic surgical methods. As an example, the screws and pegs disclosed herein can be used to fix prosthetic components (e.g., a bone plate, acetabular cup, glenoid component, etc.) to bone. For instance, a hole(s) can extend through the prosthetic component and any screw or peg disclosed herein can be inserted through the hole to fix the prosthetic component to the bone. In these examples, the various porous parts of the above screws and pegs can be arranged to sit within cancellous and/or cortical bone and act to improve bone ingrowth into the relevant screw or peg and improve fixation. In certain examples, therefore, the disclosed screws and pegs are suitable for use in situations where poor bone quality is observed. The disclosed screws and pegs can be used in these instances as the porous parts thereof, with or without screw threads, can improve fixation of the relevant screw or peg to bone. In addition, if screw threads are utilized in the aforementioned porous parts of the screw or peg, additional fixation characteristics can be experienced while not sacrificing bone ingrowth (e.g., since porosity is present on the thread itself and/or the interstitial spaces between threads, as discussed above).

Another application for certain of the screws disclosed herein, such as screw 10, is in trauma applications. For instance, certain versions of screw 10 can be used in trauma applications as compression screws to reduce fractures and bring bone parts defining the fracture(s) together. These versions of screw 10 typically include threads of differing pitches in different areas of shaft 12, which can facilitate compression of bone parts across a fracture. As an example, some versions of screw 10 have coarser threads disposed in a distal section of shaft 12 and finer threads disposed in a proximal section of shaft 12. These versions of screw 10 can act to cause compression across a fracture and bring bone parts together. In particular, the coarser threads can advance faster than the finer threads and act to pull a distal bone fragment towards a proximal bone fragment. According to the above examples, these versions of screw 10 can have a continuous, variable pitch thread or alternatively can have a coarse thread in a distal section of shaft 12, an unthreaded or smooth intermediate section, and a finer thread in a proximal section of shall 12. Further, the unthreaded or smooth intermediate section of screw 10 can be formed of porous OsseoTi®, and can be arranged to straddle the fracture(s) line and/or reside in natural cancellous bone so that appropriate bone ingrowth occurs in the trauma repair. In addition, the porous threads of screw 10 (e.g., covered with OsseoTi®) can also reside in natural cancellous bone and/or cortical bone to facilitate bone ingrowth. Thus, examples of screw 10 disclosed herein can be used in trauma applications, such as fracture repair. The porosity of screw 10, in particular its porous threads, can act to cause positive bone ingrowth into screw 10 and improved its usability as a fracture-repair device.

Another application for the screws and/or pegs disclosed herein is in spinal applications. For instance, any of the screws or pegs disclosed herein can be used with a cortical bone plate or as a pedicle screw for use in connecting spinal rods to adjacent vertebral bodies. In the case of a pedicle screw, any of the aforementioned screws or pegs can be designed with a head 14, 114, 214, 314, 414, 514 that can be received in a tulip part of the pedicle screw. Such a screw or peg can be designed so that shaft 12, 112, 212, 312, 412, 512 is polyaxially movable relative to the tulip portion of the pedicle screw, and is capable of being locked (e.g., via a set screw) at a specific angle relative to the tulip portion. Prior to locking (e.g., with a set screw), a suitable rod or other orthopedic implant capable of spanning adjacent vertebral bodies can be connected to one (1) or more of the pedicle screws. Thus, the screws and pegs can be used as pedicle screws and attached to a rod other orthopedic device capable of spanning two (2) or more vertebral bodies so as to be able to secure the bodies in position relative to each other, for example in the case of a fusion procedure. If a fusion procedure is being conducted, a suitable intervertebral implant and/or bone graft can be placed in the intervertebral space and the pedicle screws of the above examples used to fix the adjacent vertebral bodies to help affect stable fusion. Pedicle screws incorporating the features of the above-discussed screws and/or pegs can experience greater fixation in combination with positive bone ingrowth due to the porous features on the disclosed screws and/or pegs.

Certain of the screws disclosed herein, such as screw 10, can also be used in arthrodesis procedures to fuse joints. Screw 10 can be designed to have cortical-threaded sections where appropriate, and/or cancellous-threaded sections where appropriate, with or without porosity as discussed above on the thread itself and/or in the interstitial spaces between threads. Such a screw 10 can engage cancellous and/or cortical bone portions (e.g., in the context of an arthrodesis procedure). As mentioned above, cancellous threads are characterized by a coarser pitch and cortical threads are characterized by a finer pitch (e.g., a pitch of anywhere between about).

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. A bone screw comprising:
a shaft having a thread, the thread having a thread core formed of a first biocompatible material, wherein the thread defines a root and a crest, a proximal thread face is disposed between the root and the crest on a first side of the thread, and a distal thread face is disposed between the root and the crest on a second side of the thread; and
a porous layer of a second biocompatible material covering only part of at least one of the proximal thread face or distal thread face of the thread, wherein a portion of the thread core defines the crest of the thread, and the porous layer of the second biocompatible material is thinner in the area of the crest as compared to other areas of the porous layer of the second biocompatible material.

2. The bone screw of claim 1, wherein the first biocompatible material is a non-porous metal or metal alloy, and the thread core is formed entirely of the first biocompatible material.

3. The bone screw of claim 1, wherein interstitial spaces are formed between adjacent crests of the thread and at least some of the interstitial spaces include a porous layer of the second biocompatible material.

4. The bone screw of claim 1, wherein thy: second biocompatible material has a porous architecture.

5. The bone screw of claim 1, wherein the shaft comprises a non-porous core formed of the first biocompatible material.

6. The bone screw of claim 1, further comprising a threaded head.

7. The bone screw of claim 1, wherein the shaft has a proximal section, an intermediate section, and a distal section, and wherein the proximal section is threaded with a thread having a first pitch, the intermediate section is unthreaded, and the distal section is threaded with a thread having a second pitch that is greater than the first pitch.

8. A bone screw comprising:
a shaft having a thread, the thread having a thread core formed of a first biocompatible material, wherein the thread defines a root and a crest, a proximal thread face is disposed between the root and the crest on a first side of the thread, and a distal thread face is disposed between the root and the crest on a second side of the thread; and
a porous layer of a second biocompatible material covering only part of the proximal thread face or distal thread face of the thread, wherein the shaft has a proximal section, an intermediate section, and a distal section and wherein the proximal section is threaded with a thread having a first pitch, the intermediate section is unthreaded, and the distal section is threaded with a thread having a second pitch that is greater than the first pitch, and wherein the intermediate section is at least partly covered by a porous layer of the second biocompatible material.

9. The bone screw of claim 8, wherein a portion of the thread core defines the crest of the thread, and the crest is exposed and not covered with a porous layer of the second biocompatible material so as to be configured to contact and dig into bone.

10. A bone screw comprising:
a core formed of a first biocompatible material, the core having a distal threaded section, an intermediate section, and a proximal head section, wherein the core of at least the distal threaded section defines a thread having a thread core formed of the first biocompatible material, wherein the thread defines a root and a crest, a proximal thread face is disposed between the root and the crest on a first side of the thread, and a distal thread face is disposed between the root and the crest on a second side of the thread; and
a porous sleeve covering the intermediate section of the core, the porous sleeve being composed of a second biocompatible material that has a porous architecture;
wherein the distal threaded section has a porous layer of the second biocompatible material covering only part of at least one of the proximal thread face or distal thread face of the thread, wherein a portion of the thread core defines the crest of the thread, and the porous layer of the second biocompatible material is thinner in the area of the crest as compared to other areas of the porous layer of the second biocompatible material.

11. The bone screw of claim 10, wherein the first biocompatible material is a non-porous metal or metal alloy, or is a metal or metal alloy with a porosity that is lower than a porosity of the porous sleeve.

12. The bone screw of claim 10, wherein the proximal head section defines a first diameter, the intermediate section defines a second diameter, and the distal threaded section defines a third diameter representing an outer diameter of the threads in the distal threaded section, and wherein the second diameter is smaller than the first and third diameters.

13. The bone screw of claim 12, wherein the porous sleeve defines an inner dia er that is smaller than the first and third diameters, and the core is monolithic.

14. The bone screw of claim 10, wherein the porous sleeve is retained on the core between a first step defined by a proximal-most thread of the distal threaded section, and a second step formed adjacent the proximal head section.

15. The bone screw of claim 10, wherein the core is a monolithic core formed by way of an additive manufacturing process.

16. The bone screw of claim 10, wherein the core is a multi-part core, a first part of the core that includes the proximal head section being attached to a second part of the core that has the distal threaded section.

17. A method of manufacturing a bone screw comprising:
forming a core having a section with a thread via additive manufacturing, the core being composed of a first biocompatible material, wherein the thread defines a root and a crest, a proximal thread face is disposed between the root and the crest on a first side of the thread, and a distal thread face is disposed between the root and the crest on a second side of the thread;

covering only part of at least one of the proximal thread face or distal thread face, by way of additive manufacturing, with a porous layer of a second biocompatible material;

further comprising covering anywhere between about 10-90% of at least one of the proximal thread face or distal thread face, by way of additive manufacturing, with the porous layer of the second biocompatible material and further covering; and further comprising covering the crest of the thread with the porous layer of the second biocompatible material with the second biocompatible material being thinner in the area of the crest as compared to other areas of the porous layer having the second biocompatible material.

18. The method of claim 17, wherein a portion of the crest of the thread is exposed and not covered by the porous layer of the second biocompatible material.

19. The method of claim 17, wherein the second biocompatible material has a porous architecture.

20. The method of claim 17, wherein the core defines interstitial spaces between adjacent crests of the thread, and the method further comprises covering part of a first of the interstitial spaces with a porous layer of the second biocompatible material using additive manufacturing.

* * * * *

UNITED STATES PATENT AND TRADEMARK OFFICE
CERTIFICATE OF CORRECTION

PATENT NO. : 10,675,074 B2
APPLICATION NO. : 15/877769
DATED : June 9, 2020
INVENTOR(S) : Roby et al.

It is certified that error appears in the above-identified patent and that said Letters Patent is hereby corrected as shown below:

In the Claims

In Column 13, Line 45, in Claim 4, delete "thy:" and insert --the-- therefor

In Column 14, Line 3, in Claim 8, after "section", insert --,--

In Column 14, Line 49, in Claim 13, delete "dia er" and insert --diameter-- therefor Signed and Sealed this
Third Day of September, 2024

Katherine Kelly Vidal
*Director of the United States Patent and Trademark Office*